United States Patent [19]

White et al.

[11] 4,424,401

[45] Jan. 3, 1984

[54] AROMATIZATION OF ACETYLENE

[75] Inventors: Noam White, Elsternwick; Douglas A. Kagi, Windsor; Jack G. Creer, Upwey; Peter Tsai, Parkville, all of Australia

[73] Assignees: The Broken Hill Proprietary Company Limited; Commonwealth Scientific; Industrial Research Organisation, all of Australia

[21] Appl. No.: 290,317

[22] Filed: Aug. 5, 1981

[30] Foreign Application Priority Data

Aug. 12, 1980 [AU] Australia ............................... PE4987
Jan. 27, 1981 [AU] Australia ............................... PE7375

[51] Int. Cl.$^3$ .............................................. C07C 6/00
[52] U.S. Cl. ..................................... 585/416; 585/14
[58] Field of Search ................................... 585/14, 416

[56] References Cited

U.S. PATENT DOCUMENTS

| 3,176,045 | 3/1965 | Jenny ............................... 585/416 X |
| 3,760,024 | 9/1973 | Cattanach ............................ 208/120 |
| 3,775,501 | 11/1973 | Kaeding et al. ..................... 260/673 |
| 3,790,471 | 2/1974 | Argauer et al. ...................... 208/111 |
| 3,894,103 | 7/1975 | Chang et al. .................... 208/141 X |
| 4,009,219 | 2/1977 | Tamers ............................ 585/416 X |
| 4,150,062 | 4/1979 | Garwood et al. .................... 208/71 |

FOREIGN PATENT DOCUMENTS 1211973 11/1970 United Kingdom .

Primary Examiner—Thomas A. Waltz
Attorney, Agent, or Firm—Murray & Whisenhunt

[57] ABSTRACT

A process for production of hydrocarbons useful as fuels, comprises contacting a feed stream containing acetylene with a zeolite catalyst, whereby a reaction product containing said hydrocarbons is obtained. In a preferred embodiment the feed stream contains acetylene in admixture with one or more other compounds, for example inert gases, water, hydrogen, methane, ethane, and alcohols.

14 Claims, No Drawings

AROMATIZATION OF ACETYLENE

This invention relates to the production of hydrocarbon compounds, including aromatic hydrocarbons, useful as fuels.

The production of aromatics is of particular importance because lighter aromatics which boil in the normal gasoline range have very high octane numbers and are therefore excellent gasoline blend stocks. In addition, benzene, toluene and xylene are important for their chemical uses and as chemical feedstocks.

The uncertain availability and fluctuating price of petroleum for gasoline and chemical manufacture has directed increased attention to the potential of methane (natural gas) and coal as major alternative raw materials for these uses. Using the route developed by Mobil, the production of aromatic gasoline from natural gas and coal depends upon the production of methanol as an intermediate, and routes to methanol from coal and methane depend on the production of synthesis gas (hydrogen and carbon monoxide mixture).

It has long been known that coal can be converted via gasification to mixtures of carbon monoxide and hydrogen (synthesis gas). The carbon monoxide-hydrogen mixture may be adjusted in ratio using the water gas shift reaction followed by removal of $CO_2$ and methanol can then be produced.

The gasification reaction may be represented as:

$$coal + H_2O \rightarrow H_2 + CO (also\ CH_4 + CO_2)$$

$$coal + O_2 \rightarrow CO_2$$

The latter reaction is required to generate heat for the gasification reaction and results in carbon loss.

The water gas shift reaction is $$H_2O + CO \rightarrow H_2 + CO_2$$

Methanol may then be produced by the following reactions:

$$2H_2 + CO \rightarrow CH_3OH$$

$$3H_2 + CO_2 \rightarrow CH_3OH + H_2O$$

Overall products are methanol and carbon dioxide. It has also been known that synthesis gas can be produced from methane by steam reforming, in accordance with the reactions $$CH_4 + H_2O \rightarrow 3H_2 + CO$$

$$CH_4 + 2O_2 \rightarrow CO_2 + 2H_2O$$

Some methane is reacted with oxygen to generate heat for the steam reforming and this results in carbon loss.

Since methanol conversion requires the reaction $$2H_2 + CO \rightarrow CH_3OH$$

the reforming step produces a deficiency of carbon for this conversion and this deficiency is usually made up by the addition of carbon dioxide. This carbon dioxide is available from the combustion of the methane. However, in practice there is wastage of carbon as carbon dioxide.

The use of crystalline aluminosilicate zeolites as catalysts for the conversion of methanol to hydrocarbon products has been proposed in the Mobil process. This produces a hydrocarbon product of the following approximate composition:

|  | Wt % |
| --- | --- |
| methane + ethane + ethylene | 1.5 |
| propane | 5.6 |
| isobutane | 9.0 |
| n-butane | 2.9 |
| propylene + butenes | 4.7 |
| $C_5$ + nonaromatics | 49.0 |
| aromatics | 27.3 |
|  | 100.0 |
| $C_5$ + fraction | 76.3 |

The most valuable products from this Mobil process are the aromatics, but these comprise only about 30% of total products.

Existing technology has thus established a route from either coal or natural gas to aromatic gasoline via methanol; but the abovementioned processes have serious shortcomings.

The disadvantage of the use of coal as the raw material is the very high cost of plant for the coal gasification and the introduction of oxygen into the process produces loss of carbon as carbon dioxide.

The disadvantage of the route from methane via methanol is the loss of methane to carbon dioxide and water due to the introduction of oxygen.

A further disadvantage of the Mobil methanol to gasoline conversion over zeolite catalysts is the low proportion (about 30%) of valuable high octane aromatic product and the consequent high proportion of less valuable lower octane materials. Yet another disadvantage is that water produced during the methanol conversion is entrained in the product, so requiring a later separation step. In addition, any unreacted methanol is difficult and expensive to separate from the product stream, so operating conditions need to be biased towards maximum conversion of methanol at the expense of better selecting the composition of the product stream. Also, there is substantial loss of weight due to the elimination of water.

It is an object of this invention to provide a novel process for production of useful hydrocarbon fuels, including aromatic ring compounds.

In a general aspect the invention provides a process for the production of useful hydrocarbon fuels, including aromatic ring compounds, from acetylene, either alone or in admixture with other compounds.

In accordance with the invention it has been found that useful hydrocarbon fuels including aromatic ring compounds may be produced by contacting acetylene either alone or in admixture with certain other compounds, with a zeolite catalyst. An advantage of this process over the conversion of methanol is that any unreacted acetylene is far easier to separate from the product stream than is methanol, so making more viable a trade-off of a lower degree of conversion for a more desirable liquid product mix.

The preferred catalysts for use in the process of this invention are zeolites with a crystal framework structure similar to the ZSM-5 type zeolites. Zeolite catalysts of this type are disclosed in U.S. Pat. No. 3,702,886. Other zeolites of the ZSM-5 type are disclosed in Australian Patent Specification No. AU-A 35237/78. Another zeolite with a framework structure similar to that of ZSM-5 is described in U.S. Pat. No. 4,104,294 and in an article by E. M. Flanigen et al in Nature, vol. 27; p.512, 1978, and is known as silicalite. One characteristic of these zeolites is their silica to alumina ratio. The preferred range of silica to alumina disclosed in U.S. Pat. No. 3,702,886 is between 5 and 100. Silicalite has a much higher silica to alumina ratio. In U.S Pat. No. 4,104,294, the silica to alumina ratio has a lower limit of 800. Zeolite catalysts with a crystal framework structure similar to the ZSM-5 type zeolites may be prepared with a very large silica to alumina ratio, but in practice it is believed that these catalysts are never entirely free of alumina, even though no alumina may be deliberately added during preparation thereof.

In the course of our continuing research into the catalytic production of useful hydrocarbon fuels from starting materials including acetylene, we have now found that advantages are obtained by use of a zeolite catalyst having a crystal framework structure similar to the ZSM-5 type zeolites, and having a high silica to alumina ratio, preferably at least about 100. Improved catalyst life is one of the advantages achieved by the process of the present invention.

A preferred embodiment of this invention comprises contacting a mixture of gaseous acetylene and one or more other gases (which may be inert, for example helium and/or nitrogen) with the preferred zeolite catalysts, or alternatively, in a further embodiment the feed may consist of gaseous acetylene and water. Water may be substituted in this process by alcohols such as methanol, ethanol or higher alcohols. Further, contact of a gaseous mixture of acetylene and methane or ethane or ethylene or hydrogen, or acetylene alone, with the preferred catalyst produces a useful product containing a mixture of aromatic compounds.

Processes are available for the conversion of methane to acetylene and for the conversion of coal to acetylene. Processes may be chosen which are electrically based and suffer no loss of feedstock carbon due to the introduction of oxygen as do the synthesis gas processes outlined above. Thus economic sources of acetylene for use in the process of the present invention are available and it is to be expected that further developments in acetylene production technology from coal or methane will accelerate the adoption of acetylene as a key intermediate in future fuel technology. An advantage of the present invention is that hydrogen used in the process could be obtained as a by-product of methane to acetylene conversion.

The catalysts employed in this invention may be in the hydrogen form and/or they may be exchanged and/or may be impregnated to contain a metal cation complement. Further the catalyst may be modified by the inclusion of one or more metals other than aluminum, e.g. iron, in the crystal structure. It is normally desirable to calcine the catalyst before use.

The metal cations that may be present may include one or more cations of the metals of Group I through to Group VIII of the periodic table.

The zeolite, with or without impregnation may be combined, dispersed or otherwise intimately mixed with an inorganic oxide matrix in such proportions that the resulting product contains 1% to 95% by weight of the zeolite in the final product. Matrices which impart desirable properties to the zeolite such as increased strength and attrition resistance are preferred.

The process can utilize either a fixed or fluidized bed of catalyst.

In a preferred embodiment of the invention the catalyst is a crystalline aluminosilicate zeolite having a silica to alumina ratio of 35 to 500, preferably having a silica to alumina ratio of 80 to 300.

In a preferred embodiment of the invention a process comprises converting acetylene, in the presence of one or more other gases as noted above, to a predominantly aromatic mixture in the presence of a catalyst as described above at an elevated temperature up to 550° C., preferably about 260°–450° C., carrying out said conversion at between 0.5 and 50 atmospheres, and a weight hourly space velocity (WHSV) of 0.1 to 20 $hr^{-1}$, with the other gas comprising from 0 to 95 volume percent of the feed stream.

EXPERIMENTAL

To illustrate the preparation of the catalyst type the following experimental procedure has been included. Fifty six gram of sodium silicate solution (29.1 wt.% $SiO_2$, 9.1 wt. % $Na_2O$) was mixed with 193.6 gram distilled water. To this solution, 1.04 gram of sodium hydroxide was added, followed by the addition of 7.04 gram of tetra n-propyl ammonium bromide. This mixture was thoroughly mixed and 4.9 gram of 98 weight percent sulphuric acid added. After further vigorous mixing the material was placed in a pyrex vessel inside a stainless steel pressure vessel, placed in an oven and held at 175° C. for 48 hours. The product from the reaction vessel was filtered; thoroughly washed with distilled water, dried at 110° C. overnight and calcined at 500° C. for 16 hours. On cooling a portion of the product was washed with 0.3 M hydrochloric acid at 100° C. for 16 hours. The material was then filtered, washed and dried. X-ray diffraction showed that the material gave a diffraction pattern very similar to that typical of ZSM-5. The catalyst was found to contain a small amount of alumina, although no deliberate addition of alumina was made. The source of this alumina is not definitely known, but it is though that it may be derived from impurities in the sodium silicate solution. The silica to alumina ratio in this catalyst was 120.

To illustrate the preparation of a catalyst modified by the inclusion of a metal other than aluminium in the crystal lattice, the experimental procedure for preparation of an iron modified zeolite catalyst (Fe-ZSM-5) was identical to that given above except that 7.44 gram $Fe(NO_3)_3.9H_2O$ was added with the sulphuric acid in the reaction mixture.

EXAMPLES

The following examples are illustrative of this invention and are not to be considered to be limiting on the scope thereof.

In each example the feed stream was passed through an electrically heated reactor tube containing an appropriate aluminosilicate zeolite which had been pelletized and crushed to a particle size of 80-100 mesh. The total pressure was usually one atmosphere and the weight of catalyst was 0.1 gram. The reactor effluent was analysed by gas chromatography (GC) using a 4 m × 3 mm silicone OV101 column in a temperature programmed mode. Parts and percentages are by weight.

In each table BTX is the sum of Benzene, Toluene and Xylenes; $C_{10}+$ is the aromatic of carbon number $\geq 10$; and $C_9$ is aromatics of carbon number = 9.

EXAMPLES 1-6

Acetylene and two diluent gases were contacted with zeolites having different silica/alumina ratios. A rise in temperature increases the acetylene conversion and alters the effluent composition as shown in Table 1.

TABLE 1

| | Variation of $SiO_2/Al_2O_3$ (50-120) Variation of Temperature (300-400° C.) | | | | | |
|---|---|---|---|---|---|---|
| EXAMPLE | 1 | 2 | 3 | 4 | 5 | 6 |
| FEED   $C_2H_2$ | 0.3 | 0.3 | 0.3 | 0.3 | 0.3 | 0.3 |
| (cc/min)   $H_2$ | 1.6 | 1.6 | 1.6 | 1.6 | 1.6 | 1.6 |
| He | 1.9 | 1.9 | 1.9 | 1.9 | 1.9 | 1.9 |
| CATALYST | H—ZSM-5 | H—ZSM-5 | H—ZSM-5 | H—ZSM-5 | H—ZSM-5 | H—ZSM-5 |
| $SiO_2/Al_2O_3$ | 50 | 50 | 80 | 80 | 120 | 120 |
| TEMP (°C.) | 300 | 400 | 300 | 400 | 300 | 400 |
| CONVERSION (% of $C_2H_2$) | 10.2 | 36.4 | 11.5 | 57.3 | 11.0 | 49.4 |
| MHSV ($hr^{-1}$) of $C_2H_2$ | 0.2 | 0.2 | 0.2 | 0.2 | 0.2 | 0.2 |
| PRODUCTS (%) | | | | | | |
| NON-AROMATICS | 13.7 | 23.5 | 33.8 | 39.8 | 33.8 | 41.3 |
| BTX | 43.7 | 35.0 | 31.3 | 41.2 | 23.9 | 30.2 |
| $C_9$ | 25.6 | 18.1 | 16.1 | 10.1 | 15.7 | 10.1 |
| $C_{10}^+$ | 17.0 | 23.3 | 18.9 | 8.8 | 26.6 | 18.3 |

BTX: Benzene, Toluene, Xylenes
$C_{10}^+$: Aromatics of carbon number $\geq 10$
$C_9$: Aromatics of carbon number $= 9$

EXAMPLES 6-8

Acetylene was subjected to three experiments involving dilution with hydrogen, helium and/or water. Comparison of yields and product distribution for the same crystalline aluminosilicate catalyst were made. The results are summarized in Table 2.

TABLE 2

| | Variation of Feed ($H_2O$, $H_2$, He) | | |
|---|---|---|---|
| EXAMPLE | 6 | 7 | 8 |
| FEED   $C_2H_2$ (cc/min) | 0.3 | 0.3 | 0.3 |
| $H_2$ | 1.6 | 1.6 | 6.0 |
| He | 1.9 | 1.9 | — |
| $H_2O$ (g/min) | | 0.013 | 0.013 |
| CATALYST | H—ZSM-5 | H—ZSM-5 | H—ZSM-5 |
| ($SiO_2/Al_2O_3$) | 120 | 120 | 120 |
| TEMP (°C.) | 400 | 400 | 400 |
| CONVERSION (% of $C_2H_2$) | 49.4 | 68.7 | 85.4 |
| MHSV ($hr^{-1}$) of $C_2H_2$ | 0.2 | 0.2 | 0.2 |
| PRODUCTS (%) | | | |
| NON-AROMATICS | 41.3 | 23.0 | 24.1 |
| BTX | 30.2 | 41.5 | 51.9 |
| $C_9$ | 10.1 | 8.0 | 8.9 |
| $C_{10}^+$ | 18.3 | 27.0 | 13.6 |

EXAMPLES 9-10

Table 3 illustrates the variation in product distribution of the effluent with an increase in the space velocity over at H-ZSM-5 type catalyst at similar conversion levels.

TABLE 3

| | Variation of Space Velocity | |
|---|---|---|
| EXAMPLE | 9 | 10 |
| FEED   $C_2H_2$ (cc/min) | 0.3 | 1.0 |
| $H_2$ | 1.8 | 7.8 |
| $N_2$ | 2.3 | 8.4 |
| CATALYST | H—ZSM-5 | H—ZSM-5 |
| ($SiO_2/Al_2O_3$) | 66.1 | 66.1 |
| TEMP (°C.) | 400 | 400 |
| CONVERSION (% of $C_2H_2$) | 21.8 | 21.1 |
| MHSV ($hr^{-1}$) of $C_2H_2$ | 0.2 | 0.7 |
| PRODUCTS (%) | | |
| NON-AROMATICS | 67.5 | 52.2 |
| BTX | 20.7 | 12.8 |
| $C_9$ | 5.4 | 5.6 |
| $C_{10}^+$ | 6.3 | 29.7 |

EXAMPLE 11-18

Acetylene and a diluent were passed over zeolites with increasing silica/alumina ratio. The percentage conversion of the acetylene and its product distribution under specific operating condition are shown in Table 4.

TABLE 4

| | Acetylene and Helium in Feed | | | | | | | |
|---|---|---|---|---|---|---|---|---|
| EXAMPLE | 11 | 12 | 13 | 14 | 15 | 16 | 17 | 18 |
| FEED   $C_2H_2$ | 0.5 | 0.5 | 0.5 | 0.5 | 0.5 | 0.5 | 0.7 | 0.7 |
| (cc/min)   $H_2$ | — | — | — | — | — | — | — | — |
| He | 2.9 | 2.9 | 2.9 | 2.9 | 3.9 | 3.9 | 3.6 | 3.6 |
| CATALYST | H—ZSM-5 | H—ZSM-5 | H—ZSM-5 | H—ZSM-5 | H—ZSM-5 | H—ZSM-5 | H—ZSM-5 | H—ZSM-5 |
| $SiO_2/Al_2O_3$ | 50 | 50 | 120 | 120 | 206 | 206 | 486 | 486 |
| TEMP (°C.) | 297 | 400 | 300 | 400 | 300 | 400 | 300 | 400 |
| CONVERSION (% of $C_2H_2$) | 29.4 | 40.7 | 4.7 | 45.1 | 11.4 | 34.7 | 4.5 | 17.2 |
| MHSV ($hr^{-1}$) of $C_2H_2$ | 0.4 | 0.4 | 0.4 | 0.4 | 0.4 | 0.4 | 0.5 | 0.5 |
| PRODUCTS (%) | | | | | | | | |
| NON-AROMATICS | 1.2 | 3.7 | 8.1 | 11.3 | 5.9 | 1.0 | 13.0 | 1.7 |
| BTX | 19.6 | 31.5 | 40.4 | 60.4 | 8.3 | 22.4 | 10.0 | 11.7 |
| $C_9$ | 13.4 | 11.1 | 19.8 | 10.5 | 7.2 | 12.7 | 5.8 | 6.3 |

TABLE 4-continued

| EXAMPLE | Acetylene and Helium in Feed | | | | | | | |
|---|---|---|---|---|---|---|---|---|
| | 11 | 12 | 13 | 14 | 15 | 16 | 17 | 18 |
| $C_{10}^+$ | 65.7 | 53.7 | 31.8 | 17.9 | 78.8 | 64.0 | 71.3 | 80.4 |

EXAMPLES 19-20

Catalyst activity decreases with time as shown by yields and product distributions in Table 5.

TABLE 5

| | Catalyst Activity with Time | |
|---|---|---|
| EXAMPLE | 19 | 20 |
| FEED $C_2H_2$ (cc/min) | 0.5 | 0.5 |
| $H_2$ | 1.0 | 1.0 |
| He | 6.0 | 6.0 |
| CATALYST | H—ZSM-5 | H—ZSM-5 |
| ($SiO_2/Al_2O_3$) | 120 | 120 |
| TEMP (°C.) | 400 | 400 |
| | (after 15 min) | (after 220 min) |
| CONVERSION (% of $C_2H_2$) | 35.5 | 19.0 |
| MHSV (hr$^{-1}$) of $C_2H_2$ | 0.4 | 0.4 |
| PRODUCTS (%) | | |
| NON-AROMATICS | 13.1 | 4.5 |
| BTX | 55.5 | 28.1 |
| $C_9$ | 25.2 | 31.3 |
| $C_{10}^+$ | 6.1 | 36.0 |

EXAMPLES 21-25

Table 6 demonstrates the effectiveness of a catalyst in which the presence of a metal other than aluminium has been included in the structure of the ZSM-5 zeolite. Further, that the use of different liquid feeds can alter the yield and distribution of aromatized product in the effluent.

TABLE 6

| | Fe replacing Al in the Zeolite Framework | | | | |
|---|---|---|---|---|---|
| EXAMPLE | 21 | 22 | 23 | 23 | 25 |
| FEED $C_2H_2$ (cc/min) | 0.4 | 0.4 | 0.4 | 0.4 | 0.4 |
| $H_2$ | 2.2 | 2.2 | 2.2 | 2.2 | 2.2 |
| $N_2$ | 3.0 | 3.0 | 3.0 | 3.0 | 3.0 |
| $H_2O$ (g/min) | | 0.005 | | 0.005 | |
| MeOH | | | | | 0.005 |
| CATALYST | Fe—ZSM-5 | Fe—ZSM-5 | Fe—ZSM-5 | Fe—ZSM-5 | Fe—ZSM-5 |
| $SiO_2/Al_2O_3$ | 140 | 140 | 140 | 140 | 140 |
| TEMP (°C.) | 300 | 300 | 400 | 400 | 400 |
| CONVERSION (% of $C_2H_2$) | 56.3 | 30.0 | 86.9 | 64.2 | 93.0 |
| MHSV (hr$^{-1}$) of $C_2H_2$ | 0.3 | 0.3 | 0.3 | 0.3 | 0.3 |
| PRODUCTS (%) | | | | | |
| NON-AROMATICS | 9.2 | 21.5 | 4.4 | 28.3 | 2.4 |
| BTX | 31.7 | 27.3 | 30.6 | 24.3 | 35.1 |
| $C_9$ | 10.1 | 16.0 | 10.7 | 13.6 | 12.2 |
| $C_{10}^+$ | 48.3 | 35.7 | 54.3 | 33.0 | 50.3 |

The present specification incorporates by this cross-reference the entire contents of our Australian provisional specification Nos. PE 4987 and PE 7375 filed on Aug. 12, 1980 and Jan. 27, 1981 respectively.

We claim:

1. A process for producing a hydrocarbon stream containing predominately aromatic compounds, said process comprising contacting a feed stream containing acetylene with a crystalline zeolite catalyst having a silica to alumina molar ratio of 35 to 500 or a zeolite catalyst having a crystal framework structure similar to the ZSM-5 type zeolites and having a silica to alumina molar ratio of at least 100, at a temperature of about 260° to 550° C., a pressure between 0.5 and 50 atmospheres, and a weight hourly space velocity of 0.1 to 20 hr$^{-1}$ to convert the acetylene to a predominately aromatic mixture, wherein the process can tolerate the presence of water and hydrogen in the feed stream.

2. A process which comprises contacting a feed stream containing acetylene with a crystalline zeolite catalyst having a silica to alumina molar ratio of 35 to 500 or a zeolite catalyst having a crystal framework structure similar to the ZSM-5 type zeolites and having a silica to alumina molar ratio of at least 100 at a temperature of 260° C. to 550° C., pressure between 0.5 and 50 atmospheres, and a weight hourly space velocity of 0.1 to 20 hr$^{-1}$, to produce a reaction product containing aromatic hydrocarbons, said feed stream containing acetylene either alone or in admixture with other gases comprising up to 95 volume percent of said feed stream.

3. Process according to claim 1 or claim 2 in which the feed stream consists essentially of acetylene.

4. A process according to claim 1 or claim 2 in which the aromatic rich hydrocarbon stream contains at least 10% (wt) of benzene, toluene or xylene or mixture thereof.

5. A process according to claim 1 or claim 2 in which the feed stream comprises acetylene in admixtures with one or more compounds selected from the group consisting of inert gases, hydrogen, methane, ethane, alcohols and water.

6. A process according to claim 5 in which the feed stream contains at least 5 mole percent acetylene.

7. A process according to claim 1 or claim 2 in which the catalyst is a zeolite with a crystal framework structure similar to the ZSM-5 type zeolites.

8. Process according to claim 7 in which the catalyst is modified by inclusion of one or more metals other than aluminum.

9. A process according to claim 8 in which the catalyst is modified by inclusion of iron.

10. A process according to claim 1 or claim 2 in which the temperature is about 260° C. to 450° C.

11. A process according to claim 10 in which the pressure is 0.5 to 2.5 atmospheres.

12. Process according to claim 2 in which the zeolite catalyst silica to alumina ratio is 80 to 300.

13. Process of claim 1 or claim 2, wherein said feed stream also contains a member selected from the group consisting of methanol, ethanol or higher alcohols.

14. A process according to claim 1 or claim 2 in which the catalyst is the zeolite catalyst with the silica to alumina molar ratio of 35 to 500.

* * * * *

UNITED STATES PATENT AND TRADEMARK OFFICE
CERTIFICATE OF CORRECTION

PATENT NO. : 4,424,401

DATED : January 3, 1984

INVENTOR(S) : Noan White, et al.

It is certified that error appears in the above-identified patent and that said Letters Patent is hereby corrected as shown below:

In the title page of the patent, under the heading "[73] Assignees:" delete this section in its entirety and insert therefor --The Broken Hill Proprietary Company Limited; and Commonwealth Scientific and Industrial Research Organisation, both of Australia--

In TABLE 6, bridging columns 7 and 8, in the horizontal line entitled "EXAMPLE", delete "23" (second occurrence) and insert therefor --24--

Signed and Sealed this

Fifth Day of August 1986

[SEAL]

Attest:

DONALD J. QUIGG

Attesting Officer

Commissioner of Patents and Trademarks